United States Patent [19]

Michalczyk et al.

[11] Patent Number: 5,798,430
[45] Date of Patent: Aug. 25, 1998

[54] MOLECULAR AND OLIGOMERIC SILANE PRECURSORS TO NETWORK MATERIALS

[75] Inventors: Michael Joseph Michalczyk, Wilmington, Del.; Kenneth George Sharp, Landenburg, Pa.

[73] Assignee: E. I. du Pont de Nemours and Compnay, Wilmington, Del.

[21] Appl. No.: 663,834

[22] Filed: Jun. 14, 1996

Related U.S. Application Data

[60] Provisional application No. 60/000,574, Jun. 28, 1995.
[51] Int. Cl.$^6$ .................. C08G 77/00; C08G 77/24; C08G 77/60
[52] U.S. Cl. .................. 528/42; 427/387; 528/12; 528/25; 528/34; 528/35; 528/39; 528/40
[58] Field of Search .................. 427/387; 528/12, 528/25, 34, 35, 39, 40, 42

[56] References Cited

U.S. PATENT DOCUMENTS

| | | | |
|---|---|---|---|
| 2,777,870 | 1/1957 | McBee et al. | 260/448.8 |
| 2,993,925 | 7/1961 | Husted | 260/448.8 |
| 3,329,698 | 7/1967 | Popoff | 260/448.8 |
| 3,491,134 | 1/1970 | Seil et al. | 260/448.8 |
| 3,542,830 | 11/1970 | Kim et al. | 260/448.2 |
| 4,143,143 | 3/1979 | Seiler | 424/258 |
| 4,316,042 | 2/1982 | Funfschilling | 560/27 |
| 4,436,798 | 3/1984 | Shennan et al. | 430/17 |
| 4,618,689 | 10/1986 | Traver et al. | 556/425 |
| 4,652,663 | 3/1987 | Takago et al. | 549/215 |
| 4,699,988 | 10/1987 | Traver et al. | 556/415 |
| 5,026,862 | 6/1991 | Tessier et al. | 560/124 |
| 5,101,057 | 3/1992 | Satoh et al. | 556/437 |
| 5,126,420 | 6/1992 | Satoh et al. | 528/32 |
| 5,266,222 | 11/1993 | Willis et al. | 252/49.006 |
| 5,276,110 | 1/1994 | Zhou et al. | 525/479 |
| 5,312,964 | 5/1994 | Babin et al. | 560/124 |
| 5,314,731 | 5/1994 | Yoneda et al. | 428/429 |
| 5,378,790 | 1/1995 | Michalczyk et al. | 528/35 |
| 5,548,051 | 8/1996 | Michalczyk et al. | 528/15 |
| 5,684,111 | 11/1997 | Michalczyk et al. | 528/27 |

FOREIGN PATENT DOCUMENTS

| | | | |
|---|---|---|---|
| 0 232 024 | 8/1987 | European Pat. Off. | C08L 83/06 |
| 0 496 597 | 7/1992 | European Pat. Off. | C07F 7/08 |
| 2-22372 | 1/1990 | Japan | C09D 183/02 |

OTHER PUBLICATIONS

Seyferth D. et al., *Organometallics*, 13, pp. 2682–2690, 1994.

Muzafarov, A.M. et al, *Polymer Science*, 35(11), 1575–1580, 1993.

van der Made, A.W. et al., *J. Chem. Soc., Chem. Commun.*, 1400–1401, 1992.

Roovers, J. et al., *Macromolecules*, 26, 4324–4331, 1993.

Froberger, C.F., *Notes*, 25, 311–312, 1960.

Liepins, E. et al., *J. of Organometallic Chem.*, 306, 167–182, 1986.

*Primary Examiner*—James C. Housel
*Assistant Examiner*—Rodney P. Swartz

[57] ABSTRACT

The present invention pertains to molecular and oligomeric organo-silicon compounds bearing fluorine atoms, soluble in fluorinated solvents and useful as precursors to network materials.

13 Claims, No Drawings

MOLECULAR AND OLIGOMERIC SILANE PRECURSORS TO NETWORK MATERIALS

This application claims the priority benefit of U.S. Provisional Application 60/000,574, filed Jun. 28, 1995.

BACKGROUND OF THE INVENTION

This invention concerns organosilicon compounds and in particular concerns novel molecular and oligomeric organosilicon compounds bearing fluorine atoms.

Various kinds of fluorine-bearing organosilicon compounds are known in organosilicon chemistry including, for example, simple fluorine-containing alkoxysilanes such as fluoroalkoxysilanes of the formula $(R_fCH_2O)_4Si$, wherein $R_f=CF_3$ to $C_{10}F_{21}$, disclosed in U.S. Pat. No. 2,993,925; $(CF_3(CF_2)_xCX_2CH_2CH_2O)_4Si(x=0-4$ and $X=H$ or $F)$ in U.S. Pat. No. 3,491,134; and $HSi(OCH_2CF_3)_3$ and $CH_2=CHSi(OCH_2CF_3)_3$ in U.S. Pat. No. 4,652,663.

U.S. Pat. No. 5,378,790 describes more complex compounds, called "stars", of the formula $X(SiQ_3)_n$ wherein Q is $C_1$ to about $C_8$ alkoxy, $C_1$ to about $C_8$ acyloxy, or halogen. However, a fluoroalkoxy Q is not described in this patent and processes for the preparation of precursors with a fluoroalkoxy Q are not provided.

There has also been great interest in recent years in polymers with a regular, three-dimensional, treelike structure. Such polymers are called dendrimers. These tree-like molecules are the result of a controlled repetitive growth starting from a polyfunctional core. From the core, two or more identical branches emanate, each branch containing further branch sites at its end. With successive generations a fractal, ball-like structure evolves until further growth is limited by surface congestion. While most of such polymers are wholly organic, a few organosilicon dendrimers have been prepared. D. Seyferth et al., in "Synthesis of an Organosilicon Dendrimer Containing 324 Si—H Bonds", Organometallics 1994, 13, 2682–2690 describe starting with tetravinylsilane as a core molecule, a succession of alternate Pt-catalyzed hydrosilylations of all vinyl groups with $HSiCl_3$ and vinylations of all of the SiCl groups introduced with $CH_2=CHMgBr$ in tetrahydrofuran providing a divergent synthesis of four generations of polycarbosilane dendrimers in which the Si atoms are linked by $CH_2CH_2$ groups. The chlorosilane of each generation was reduced with $LiAlH_4$ to the corresponding silicon hydride. Compounds with fluorinated ends or fluoroalkoxy or alkoxy ends are not mentioned or enabled.

Applicant has prepared novel fluorine-bearing organosilicon compounds of he "star" and "dendrimer" type and novel fluorine-bearing polysilicates which are particularly useful in nonconventional sol-gel chemistry conducted in fluorinated solvents.

SUMMARY OF THE INVENTION

The present invention provides a compound of formula I $$X(Si(OC_aH_{2a}R_f)_3)_n \qquad I$$

wherein:

X is at least one organic link selected from the group consisting of:
(a) $R^1{}_mSiY_{4-m}$;

(b) ring structures

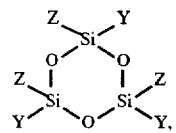

Ib(i)

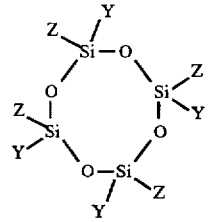

Ib(ii)

and

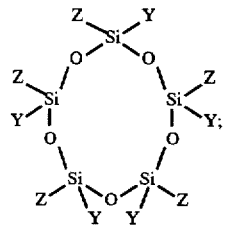

Ib(iii)

(c) $R^1{}_mSi(OSi(CH_3)_2Y)_{4-m}$;
(d) $CH_3SiY_2OSiY_2CH_3$;
(e) $Y_3SiOSiY_3$;
(f) $Y_2(CH_3)Si(CH_2)_bSi(CH_3)Y_2$;
(g) $Y_3Si(CH_2)_bSiY_3$;
(h) $Y_3SiC_6H_4SiY_3$;
(i) substituted benzene, including all isomers, selected from the group consisting of:
 (i) $C_6H_3(SiZ_{3-c}Y_c)_3$;
 (ii) $C_6H_2(SiZ_{3-c}Y_c)_4$;
 (iii) $C_6H(SiZ_{3-c}Y_c)_5$; and
 (iv) $C_6(SiZ_{3-c}Y_c)_6$; and
(j) substituted cyclohexane, including all stereoisomers, selected from the group consisting of:
 (i) $1,2-C_6H_{10}(Y)_2$; $1,3-C_6H_{10}(Y)_2$; $1,4-C_6H_{10}(Y)_2$;
 (ii) $1,2,4-C_6H_9(Y)_3$; $1,2,3-C_6H_9(Y)_3$; $1,3,5-C_6H_9(Y)_3$;
 (iii) $1,2,3,4-C_6H_8(Y)_4$; $1,2,4,5-C_6H_8(Y)_4$; $1,2,3,5-C_6H_8(Y)_4$;
 (iv) $1,2,3,4,5-C_6H_7(Y)_5$; and
 (v) $C_6H_6(Y)_6$; and
(k) $Y(CF_2)_vY$ $R_f$ has up to about 18 carbon atoms and is selected from the group consisting of:
(a) $C_1$ to about $C_{18}$ perfluoroalkyl;
(b) $-[CF_2CF(CF_3)O]_r-CF_2-CF_2-CF_3$, wherein r is an integer of at least 1;
(c) $-CF_2-(CF_2-O)_q-CF_3$, wherein q is an integer of at least 2; and
(d) $-CH_2-C(CF_3)_2-CF_2-CF_2-CF_3$;

wherein up to 50% of the fluorine of the $R_f$ group is optionally substituted with hydrogen;
a is an integer from 1 to about 10;
b is an integer from 1 to about 10;
c is 1, 2 or 3;
m is 0, 1 or 2;
n is an integer greater than or equal to 2;
v is an even integer from 2 to about 14;
$R^1$ is $C_1$ to about $C_8$ alkyl or aryl;

Y is —$(CR^2R^3)_k CR^4R^5CR^6R^7(CR^8R^9)_h$—

$R^2$ to $R^9$ are each independently hydrogen, $C_1$ to about $C_8$ alkyl, or aryl, provided that at least one of $R^4$ to $R^7$ is hydrogen;

k and h are each independently an integer from 0 to 10, provided that at least one of k or h is zero; and Z is $C_1$ to about $C_4$ alkyl, 3,3,3-trifluoropropyl, aralkyl or aryl.

The present invention also provides a compound of formula IA

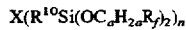
                               IA wherein:

X is at least one organic link selected from the group consisting of:
(a) $R^1_m SiY_{4-m}$;
(b) ring structures

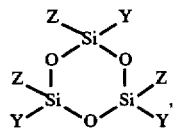
                          IA (b) (i)

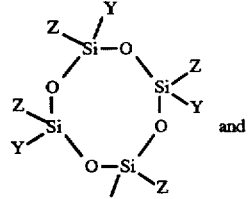
                          IA (b) (ii)

and

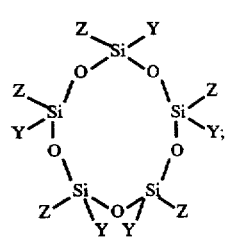
                          IA (b) (iii)

(c) $R^1_m Si(OSi(CH_3)_2 Y)_{4-m}$;
(d) $CH_3 SiY_2 OSiY_2 CH_3$;
(e) $Y_3 SiOSiY_3$;
(f) $Y_2(CH_3)Si(CH_2)_b Si(CH_3)Y_2$;
(g) $Y_3 Si(CH_2)_b SiY_3$;
(h) $Y_3 SiC_6 H_4 SiY_3$;
(i) substituted benzene, including all isomers, selected from the group consisting of:
  (i) $C_6 H_3(SiZ_{3-c} Y_c)_3$;
  (ii) $C_6 H_2(SiZ_{3-c} Y_c)_4$;
  (iii) $C_6 H(SiZ_{3-c} Y_c)_5$; and
  (iv) $C_6(SiZ_{3-c} Y_c)_6$; and
(j) substituted cyclohexane, including all stereoisomers, selected from the group consisting of:
  (i) 1,2-$C_6 H_{10}(Y)_2$; 1,3-$C_6 H_{10}(Y)_2$; 1,4-$C_6 H_{10}(Y)_2$;
  (ii) 1,2,4-$C_6 H_9(Y)_3$; 1,2,3-$C_6 H_9(Y)_3$; 1,3,5-$C_6 H_9(Y)_3$;
  (iii) 1,2,3,4-$C_6 H_8(Y)_4$; 1,2,4,5-$C_6 H_8(Y)_4$; 1,2,3,5-$C_6 H_8(Y)_4$;
  (iv) 1,2,3,4,5-$C_6 H_7(Y)_5$; and
  (v) $C_6 H_6(Y)_6$;

$R_f$ has up to about 18 carbon atoms and is selected from the group consisting of:
(a) $C_1$ to about $C_{18}$ perfluoroalkyl;

(b) —[$CF_2 CF(CF_3)O]_r$—$CF_2$—$CF_2$—$CF_3$, wherein r is an integer of at least 1;
(c) —$CF_2(CF_2 O)_q$—$CF_3$, wherein q is an integer of at least 2; and
(d) —$CH_2$—$C(CF_3)_2$—$CF_2$—$CF_2$—$CF_3$;

wherein up to 50% of the fluorine of the $R_f$ group is optionally substituted with hydrogen;

Z is $C_1$ to about $C_4$ alkyl, 3,3,3-trifluoropropyl, aralkyl or aryl;

Y is —$(CR^2 R^3)_k CR^4 R^5 CR^6 R^7(CR^8 R^9)_h$—;

$R^1$ is $C_1$ to about $C_8$ alkyl or aryl;

$R^2$ to $R^9$ are each independently hydrogen, $C_1$ to about $C_8$ alkyl or aryl, provided that at least one of $R^4$ to $R^7$ is hydrogen;

$R^{10}$ is $C_1$ to about $C_8$ alkyl or $C_a H_{2a} R_f$;

m is 0, 1 or 2;

k and h are each independently an integer from 0 to 10, provided that at least one of k or h is zero;

a is an integer from 1 to about 10;

b is an integer from 1 to about 10;

c is 1, 2 or 3; and n is an integer greater than or equal to 2.

The present invention also provides a compound of formula II

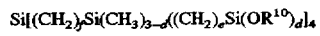
                        II wherein:

d is 1, 2 or 3;

e is an integer from 2 to about 10;

f is an integer from 2 to about 10;

$R^{10}$ is $C_1$ to about $C_8$ alkyl or $C_a H_{2a} R_f$;

a is an integer from 1 to about 10;

$R_f$ has up to about 18 carbon atoms and is selected from the group consisting of:
(a) $C_1$ to about $C_{18}$ perfluoroalkyl;
(b) —[$CF_2 CF(CF_3)O]_r$—$CF_2$—$CF_2$—$CF_3$, wherein r is an integer of at least 1;
(c) —$CF_2$—$(CF_2$—$O)_q$—$CF_3$, wherein q is an integer of at least 2; and
(d) —$CH_2$—$C(CF_3)_2$—$CF_2$—$CF_2$—$CF_3$;

wherein up to 50% of the fluorine of the $R_f$ group is optionally substituted with hydrogen.

The present invention further provides an oligomeric compound of formula III

                        III wherein:

z is a number from 0.5 to 3.0;

a is an integer from 1 to about 10; and $R_f$ has up to about 18 carbon atoms and is selected from the group consisting of:
(a) $C_1$ to about $C_{18}$ perfluoroalkyl;
(b) —[$CF_2 CF(CF_3)O]_r$—$CF_2$—$CF_2$—$CF_3$, wherein r is an integer of at least 1;
(c) —$CF_2$—$(CF_2 O)_q$—$CF_3$, wherein q is an integer of at least 2; and
(d) —$CH_2$—$C(CF_3)_2$—$CF_2$—$CF_2$—$CF_3$;

wherein up to 50% of the fluorine of the $R_f$ group is optionally substituted with hydrogen.

The present invention also provides an oligomeric compound of formula IV

                        IV wherein:

z is a number from 0.5 to 2.5;

y is an integer from 2 to about 10;

each $R^{14}$ is independently $C_1$ to about $C_8$ alkyl, $C_1$ to about $C_{10}$ carboxy, $C_1$ to about $C_{10}$ fluorocarboxy or $C_aH_{2a}R_f$;

a is an integer from 1 to about 10; and $R_f$ has up to about 18 carbon atoms and is selected from the group consisting of:
   (a) $C_1$ to about $C_{18}$ perfluoroalkyl;
   (b) —|$CF_2CF(CF_3)O$|$_r$—$CF_2$—$CF_2$—$CF_3$, wherein r is an integer of at least 1;
   (c) —$CF_2(CF_2$—$O)_q$—$CF_3$, wherein q is an integer of at least 2; and
   (d) —$CH_2$—$C(CF_3)_2$—$CF_2$—$CF_2$—$CF_3$; wherein up to 50% of the fluorine of the $R_f$ group is optionally substituted with hydrogen.

DETAILED DESCRIPTION

For the compounds of formula I, IA, II, III and IV as defined above, the $R_f$ group can be a fluoroalkyl or perfluoroalkyl group, which can be either normal or branched, and has up to about 18 carbon atoms, preferably one to eight carbon atoms, especially preferred one to three carbon atoms. Normal perfluoroalkyl groups include, for example, trifluoromethyl, perfluoroethyl, perfluoropropyl, perfluorobutyl, perfluoropentyl, perfluorohexyl, perfluorooctyl, perfluorodecyl, perfluorododecyl, and perfluorooctadecyl. $R_f$ is preferably $CF_3$, $C_2F_5$ or $C_3F_7$. Fluorine-bearing compounds of formulas I, IA, II, III and IV where $R_f$ has more than eighteen carbon atoms are considered less practical to synthesize, although such fluorosilanes would be perfectly suitable in all applications contemplated for this class of compounds. A typical suitable branched fluoroalkyl group is —$CH_2$—$C(CF_3)_2$—$CF_2$—$CF_2$—$CF_3$.

The $R_f$ groups also can be certain perfluoro(alkyleneoxy) alkyl)radicals. These include perfluoro(methylene (polymethyleneoxy)methyl) radicals (c) and perfluoro( (polyisopropyleneoxy)propyl) radicals (b).

For the compounds of formula I and IA, X is preferably (a) $R^1{}_mSiY_{4-m}$; the ring structures of formula Ib(i)–(iii) and IA(b)(i)–(iii); (c) $R^1{}_mSi(OSi(CH_3)_2Y)_{4-m}$ or (k) $Y(CF_2)_vY$. The most preferred organic link X, is where m is 0, k is 0 or 1, h is 0 or 1, and all of $R^2$ to $R^9$ are hydrogen. $R_f$ is preferably $CF_3$, $C_2F_5$ or n-$C_3F_7$. Z is preferably $CH_3$; the preferred aralkyl being benzyl and the preferred aryl being phenyl. n is preferably 2–6, most preferably 2, 3 or 4; a is preferably 1; and v is preferably 4, 6, 8 or 10, most preferably 6.

Representative examples of compounds of formula I are:
$Si(CH_2CH_2Si(OCH_2CF_3)_3)_4$;
$Si(CH_2CH_2Si(OCH_2CF_2CF_3)_3)_4$;
$Si(CH_2CH_2Si(OCH_2(CF_2)_2CF_3)_3)_4$;
$Si(OSi(CH_3)_2CH_2CH_2Si(OCH_2CF_3)_3)_4$;
$Si(OSi(CH_3)_2CH_2CH_2Si(OCH_2(CF_2)_2CF_3)_3)_4$;
$Si(OSi(CH_3)_2CH_2CH_2CH_2Si(OCH_2CF_3)_3)_4$;
cyclo-(($CH_3$)($CF_3CH_2O)_2CH_3SiCH_2CH_2)SiO)_4$;
cyclo-(($CH_3$)($CF_3CH_2O)_2CH_3SiCH_2CH_2CH_2)SiO)_4$;
cyclo-(($CH_3$)($CF_3CH_2O)_2CH_3SiCH_2CH_2CH_2)SiO)_5$;
cyclo-($CH_3(CF_3(CF_2)_2CH_2O)_3SiCH_2CH_2)SiO)_4$;
$(CF_3CH_2O)_3SiCH_2CH_2(CF_2)_6CH_2CH_2Si(OCH_2CF_3)_3$;
$(CF_3(CF_2)_2CH_2O)_3SiCH_2CH_2(CF_2)_6CH_2CH_2Si(OCH_2(CF_2)_2CF_3$; and
$(CF_3CH_2O)_3Si(CH_2)_6(CF_2)_6(CH_2)_6Si(OCH_2CF_3)_3$.

Representative examples of formula IA are:
$Si(CH_2CH_2SiCH_3(OCH_2CF_3)_2)_4$;
$Si(CH_2CH_2SiCH_3(OCH_2(CF_2)_2CF_3)_2)_4$;
$Si(OSi(CH_3)_2CH_2CH_2SiCH_3(OCH_2CF_3)_2)_4$;
$Si(OSi(CH_3)_2CH_2CH_2SiCH_3(OCH_2(CF_2)_2CF_3)_2)_4$;
$Si(OSi(CH_3)_2CH_2CH_2CH_2SiCH_3(OCH_2CF_3)_2)_4$;
$(CF_3CH_2O)_2CH_3SiCH_2CH_2(CF_2)_6CH_2CH_2SiCH_3(OCH_2CF_3)_2$;
$(CF_3(CF_2)_2CH_2O)_2CH_3SiCH_2CH_2(CF_2)_6CH_2CH_2SiCH_3(OCH_2(CF_2)_2CF_3)_2$;
$(CF_3CH_2O)_2CH_3Si(CH_2)_6(CF_2)_6(CH_2)_6SiCH_3(OCH_2CF_3)_2$;
$Si(CH_2CH_2Si(CH_2CH_2CF_2CF_3)(OCH_2CF_3)_2)_4$;
$Si(CH_2CH_2Si(CH_2CH_2CF_2CF_3)(OCH_2(CF_2)_2CF_3)_2)_4$;
$Si(OSi(CH_3)_2CH_2CH_2Si(CH_2CH_2CF_2CF_3)(OCH_2CF_3)_2)_4$;
$Si(OSi(CH_3)_2CH_2CH_2Si(CH_2CH_2CF_2CF_3)(OCH_2(CF_2)_2CF_3)_2)_4$;
$Si(OSi(CH_3)_2CH_2CH_2CH_2Si(CH_2CH_2CF_2CF_3)(OCH_2CF_3)_2)_4$;
$(CF_3CH_2O)_2(CF_3CF_2CH_2CH_2)SiCH_2CH_2(CF_2)_6CH_2CH_2Si(CH_2CH_2CF_2CF_3)(OCH_2CF_3)_2$;
$(CF_3(CF_2)_2CH_2O)_2(CF_3CF_2CH_2CH_2)SiCH_2CH_2(CF_2)_6CH_2CH_2Si(CH_2CH_2CF_2CF_3)(OCH_2(CF_2)_2CF_3)_3$;
$(CF_3CH_2O)_2(CF_3CF_2CH_2)Si(CH_2)Si(CH_2)_6(CF_2)_6(CH_2)_6Si(CH_2CF_2CF_3)(OCH_2CF_3)_2$;
cyclo-(($CH_3$)($CF_3CH_2O)_2CH_3SiCH_2CH_2)SiO)_4$;
cyclo-(($CH_3$)($CF_3CH_2O)_2CH_3SiCH_2CH_2CH_2)SiO)_4$;
cyclo-(($CH_3$)($CF_3CH_2O)_2CH_3SiCH_2CH_2CH_2)SiO)_5$; and
cyclo-(($CH_3$)($CF_3(CF_2)_2CH_2O)_2SiCH_2CH_2)SiO)_4$.

For the compounds of formula II as defined above, preferably f is 2 or 3; e is preferably 2 or 3; and $R^{10}$ is preferably $CH_2CF_3$, $CH_2C_2F_5$, or $CH_2C_3F_7$.

Representative examples of formula II are
$Si(CH_2CH_2CH_2Si(CH_3)_2CH_2CH_2CH_2Si(OCH_2CH_3)_3)_4$;
$Si(CH_2CH_2CH_2Si(CH_3)_2CH_2CH_2CH_2Si(OCH_2CF_3)_3)_4$;
$Si(CH_2CH_2CH_2SiCH_3(CH_2CH_2CH_2Si(OCH_2CH_3)_3)_2)_4$;
$Si(CH_2CH_2CH_2SiCH_3(CH_2CH_2CH_2Si(OCH_2CF_3)_3)_2)_4$; and
$Si(CH_2CH_2CH_2Si(CH_2CH_2CH_2Si(OCH_2CF_3)_3)_3)_4$.

Preferably the fluoroalkoxysilanes of formula I, formula IA and formula II are soluble in one or more fluorinated solvents. Perfluoro aliphatic (e.g., perfluoro(butyl THF)), polyfluoro aliphatic (e.g., $C_3F_7O$ $CHFCF_3$) and perfluoroaromatic (e.g., hexafluorobenzene) solvent systems can be utilized. Preferred solvents comprise perfluoro(butyl THF), e.g., "FLUORINERT" FC-75; "FLUORINERT" FC-40, a mixture of perfluoroalkylamines; perfluoro phenanthrene, e.g. "FLUTEC" PP-11; $C_3F_7O$ $CHFCF_3$, e.g., "FREON" E1; hexafluorobenzene ($C_6F_6$); perfluoromethylcyclohexane, $C_6F_{11}(CF_3)$; and perfluoro(n-ethylmorpholine). The solubility of compounds of formula I were determined in hexafluorobenzene ($C_6F_6$), perfluoro(butyl THF) (FC-75), hexane, and tetrahydrofuran (THF) and are shown below in Table I.

TABLE I

Solubility of Fluoroalkoxy Silanes

| Compound | $C_6F_6$ | FC-75 | Hexane | THF |
|---|---|---|---|---|
| $Si(CH_2CH_2Si(OCH_2CF_3)_3)_4$ | Y | N | N | Y |
| $Si(CH_2CH_2Si(OCH_2C_3F_7)_3)_4$ | Y | Y | N | N |
| $(CH_3(CH_2CH_2Si(OCH_2CF_3)_3)SiO)_4$ | Y | N | N | Y |
| $(CH_3(CH_2CH_2Si(OCH_2C_3F_7)_3)SiO)_4$ | Y | Y | N | Y |
| $Si(OSi(CH_3)_2CH_2CH_2Si(OCH_2CF_3)_3)_4$ | Y | N | N | Y |
| $Si(OSi(CH_3)_2CH_2CH_2Si(OCH_2C_3F_7)_3)_4$ | Y | Y | N | Y |
| $[(CF_2)_3CH_2CH_2Si(OCH_2CF_3)_3]_2$ | Y | N | N | Y |
| $[(CF_2)_3CH_2CH_2Si(OCH_2C_3F_7)_3]_2$ | Y | Y | N | Y |

Synthesis of the compounds of formula I and IA are afforded from hydrosilylation reactions, i.e., an addition reaction between a compound containing a Si—H group with a compound containing aliphatic unsaturation, such as an alkene, in the presence of a catalyst or free radical initiator. Precursor segments containing —CH=CH$_2$ groups react with other precursor segments which contain terminal Si—H bonds.

Either precursor segment can contain the vinyl or other unsaturated group capable of Si—H addition. For example, $Si(CH=CH_2)_4$ reacts with $HSi(OCH_2CF_3)_3$ to form the precursor $Si[CH_2CH_2Si(OCH_2CF_3)_3]_4$; $Si(CH=CH_2)_4$ reacts with $HSiCH_3(OCH_2CF_3)_2$ to form the precursor $Si(CH_2CH_2SiCH_3(OCH_2CF_3)_2)_4$; and cyclo-$[(CH_3)HSiO]_4$ reacts with $CH_2=CH$—$Si(OCH_2C_3F_7)_3$ to form the precursor cyclo-$((CH_3)(CF_3(CF_2)_2CH_2O)_3SiCH_2CH_2)SiO)_4$.

All of the following equations provide for preparation of compounds of formula I by addition of a silane across a carbon-carbon double bond for various definitions of X: (Note that preparation of compounds of formula IA proceed in like fashion except that the group $Si(R^{10})(OC_aH_{2a}R_f)_2$ replaces all instances of $Si(OC_aH_{2a}R_f)_3$.)

(a) when X is $R^1_mSiY_{4-m}$:

Eqn. 1A:
$R^1_mSi[(CR^2R^3)_kCR^4=CR^6R^7]_{4-m}+4-m\ H(CR^8R^9)_hSi(OC_aH_{2a}R_f)_3 \rightarrow R^1_mSi[(CR^2R^3)_kCR^4HCR^6R^7(CR^8R^9)_hSi(OC_aH_{2a}R_f)_3]_{4-m}$ Eqn. 1B:
$R^1_mSi[(CR^2R^3)_kH]4-m+4-m\ CR^4R^5=CR^6(CR^8R^9)_hSi(OC_aH_{2a}R_f)_3 \rightarrow R^1_mSi[(CR^2R^3)_kCR^4R^5CR^6H(CR^8R^9)_hSi(OC_aH_{2a}R_f)_3]_{4-m}$ (b) when X is a ring structure of the type Ib(i), Ib(ii) or Ib(iii), as previously defined, which can be abbreviated $(SiO)_uZ_u(YSi(OC_aH_{2a}R_f)_3)_u$, wherein u=3 for Ib(i), u=4 for Ib(ii), and u=5 for Ib(iii); then Eqn. 2A:
$(SiO)_uZ_u[(CR^2R^3)_kCR^4=CR^6R^7]_u+u\ H(CR^9R^9)_hSi(OC_aH_{2a}R_f)_3 \rightarrow (SiO)_uZ_u[(CR^2R^3)_kCR^4HCR^6R^7(CR^8R^9)_hSi(OC_aH_{2a}R_f)_3]_u$ Eqn. 2B:
$(SiO)_uZ_u[(CR^2R^3)_kH]_u+u\ CR^4R^5=CR^6(CR^8R^9)_hSi(OC_aH_{2a}R_f)_3 \rightarrow (SiO)_uZ_u[(CR^2R^3)_kCR^4R^5CR^6H(CR^8R^9)_hSi(OC_aH_{2a}R_f)_3]_u$ (c) when X is $R^1_mSi(OSi(CH_3)_2Y)_{4-m}$ Eqn. 3A:
$R^1_mSi[OSi(CH_3)_2(CR^2R^3)_kCR^4=CR^6R^7]_{4-m}+4-m\ H(CR^8R^9)_hSi(OC_aH_{2a}R_f)_3 \rightarrow R^1_mSi[OSi(CH_3)_2(CR^2R^3)_kCR^4HCR^6R^7(CR^8R^9)_hSi(OC_aH_{2a}R_f)_3]_{4-m}$ Eqn. 3B:
$R^1_mSi[OSi(CH_3)_2(CR^2R^3)_kH]_{4-m}+4-m\ CR^4R^5=CR^6(CR^8R^9)_hSi(OC_aH_{2a}R_f)_3 \rightarrow R^1_mSi[OSi(CH_3)_2(CR^2R^3)_kCR^4R^5CR^6H(CR^8R^9)_hSi(OC_aH_{2a}R_f)_3]_{4-m}$ (d) when X is $CH_3SiY_2OSiY_2CH_3$:

Eqn. 4A:
$CH_3Si((CR^2R^3)_kCR^4=CR^6R^7)_2OSi((CR^2R^3)_kCR^4=CR^6R^7)_2CH_3+4H(CR^8R^9)_hSi(OC_aH_{2a}R_f)_3 \rightarrow CH_3Si((CR^2R^3)_kCR^4HCR^6R^7(CR^8R^9)_hSi(OC_aH_{2a}R_f)_3)_2OSi((CR^2R^3)_kCR^4HCR^6R^7(CR^8R^9)_hSi(OC_aH_{2a}R_f)_3)_2CH_3$ Eqn. 4B:
$CH_3Si((CR^2R^3)_kH)_2OSi((CR^2R^3)_kH)_2CH_3+4CR^4R^5=CR^6(CR^8R^9)_hSi(OC_aH_{2a}R_f)_3 \rightarrow CH_3Si((CR^2R^3)_kCR^4R^5CR^6H(CR^8R^9)_hSi(OC_aH_{2a}R_f)_3)_2OSi((CR^2R^3)_kCR^4R^5CR^6H(CR^8R^9)_hSi(OC_aH_{2a}R_f)_3)_2CH_3$ (e) when X is $Y_3SiOSiY_3$ Eqn 5A:
$Si((CR^2R^3)_kCR^4=CR^6R^7)_3OSi((CR^2R^3)_kCR^4=CR^6R^7)_3+6H(CR^8R^9)_hSi(OC_aH_{2a}R_f)_3 \rightarrow Si((CR^2R^3)_kCR^4HCR^6R^7(CR^8R^9)_hSi(OC_aH_{2a}R_f)_3)_3OSi((CR^2R^3)_kCR^4HCR^6R^7(CR^8R^9)_hSi(OC_aH_{2a}R_f)_3)_3$ Eqn. 5B:
$Si((CR^2R^3)_kH)_3OSi((CR^2R^3)_kH)_3+6CR^4R^5=CR^6(CR^8R^9)_hSi(OC_aH_{2a}R_f)_3 \rightarrow Si((CR^2R^3)_kCR^4R^5CR^6H(CR^8R^9)_hSi(OC_aH_{2a}R_f)_3)_3OSi((CR^2R^3)_kCR^4R^5CR^6H(CR^8R^9)_hSi(OC_aH_{2a}R_f)_3)_3$ (f) when X is $Y_2(CH_3)Si(CH_2)_bSi(CH_3)Y_2$ Eqn. 6A:
$Si((CR^2R^3)_kCR^4=CR^6R^7)_2(CH_3)(CH_2)_bSi((CR^2R^3)_kCR^4=CR^6R^7)_2(CH_3)+4H(CR^8R^9)_hSi(OC_aH_{2a}R_f)_3 \rightarrow Si((CR^2R^3)_kCR^4HCR^6R^7(CR^8R^9)_hSi(OC_aH_{2a}R_f)_3)_2(CH_3)(CH_2)_bSi((CR^2R^3)_kCR^4HCR^6R^7(CR^8R^9)_hSi(OC_aH_{2a}R_f)_3)_2(CH_3)$ Eqn. 6B:
$Si((CR^2R^3)_kH)_2(CH_3)(CH_2)_bSi((CR^2R^3)_kH)_2(CH_3)+4CR^4R^5=CR^6(CR^8R^9)_hSi(OC_aH_{2a}R_f)_3 \rightarrow Si((CR^2R^3)_kCR^4R^5CR^6H(CR^8R^9)_hSi(OC_aH_{2a}R_f)_3)_2(CH_3)(CH_2)_bSi((CR^2R^3)_kCR^4R^5CR^6H(CR^8R^9)_hSi(OC_aH_{2a}R_f)_3)_2(CH_3)$ (g) when X is $Y_3Si(CH_2)_bSiY_3$:

Eqn. 7A:
$Si((CR^2R^3)_kCR^4=CR^6R^7)_3(CH_2)_bSi((CR^2R^3)_kCR^4=CR^6R^7)_3+6H(CR^8R^9)_hSi(OC_aH_{2a}R_f)_3 \rightarrow Si((CR^2R^3)_kCR^4HCR^6R^7(CR^8R^9)_hSi(OC_aH_{2a}R_f)_3)_3(CH_2)_bSi((CR^2R^3)_kCR^4HCR^6R^7(CR^8R^9)_hSi(OC_aH_{2a}R_f)_3)_3$ Eqn. 7B:
$Si((CR^2R^3)_kH)_3(CH_2)_bSi((CR^2R^3)_kH)_3+6CR^4R^5=CR^6(CR^8R^9)_hSi(OC_aH_{2a}R_f)_3 \rightarrow Si((CR^2R^3)_kCR^4R^5CR^6H(CR^8R^9)_hSi(OC_aH_{2a}R_f)_3)_3(CH_2)_bSi((CR^2R^3)_kCR^4R^5CR^6H(CR^8R^9)_hSi(OC_aH_{2a}R_f)_3)_3$ (h) when X is $Y_3SiC_6H_4SiY_3$:

Eqn. 8A:
$Si((CR^2R^3)_kCR^4=CR^6R^7)_3C_6H_4Si((CR^2R^3)_kCR^4=CR^6R^7)_3+6H(CR^8R^9)_hSi(OC_aH_{2a}R_f)_3 \rightarrow Si((CR^2R^3)_kCR^4HCR^6R^7(CR^8R^9)_h\ Si(OC_aH_{2a}R_f)_3)_3C_6H_4Si((CR^2R^3)_kCR^4HCR^6R^7(CR^8R^9)_hSi(OC_aH_{2a}R_f)_{33}$ Eqn. 8B:
$Si((CR^2R^3)_kH)_3C_6H_4Si((CR^2R^3)_kH)_3+6CR^4R^5=CR^6(CR^8R^9)_hSi(OC_aH_{2a}R_f)_3 \rightarrow Si((CR^2R^3)_kCR^4R^5CR^6H(CR^8R^9)_hSi(OC_aH_{2a}R_f)_3)_3C_6H_4CR^4R^5CR^6H(CR^8R^9)_hSi(OC_aH_{2a}R_f)_3)_3$ (i) when X is a substituted benzene structure of the type, as previously defined, which can be abbreviated $C_6H_{6-w}(SiZ_{3-c}Y_c)_w$, wherein w represents the number of substitutions on the benzene ring:

Eqn. 9A:
$w\ x\ (OC_aH_{2a}R_f)_3Si(CR^8R^9)_hH+C_6H_{6-w}[SiZ_{3-c}((CR^2R^3)_kCR^4=CR^6R^7)_c]_w \rightarrow C_6H_{6-w}[SiZ_{3-c}((CR^2R^3)_kCR^4HCR^6R^7(CR^8R^9)_hSi(OC_aH_{2a}R_f)_3)_c]_w$ Eqn. 9B:
$w\ x\ CR^4R^5=CR^6(CR^8R^9)_hSi(OC_aH_{2a}R_f)_3+C_6H_6w[SiZ_{3-c}((CR^2R^3)_kH)_c]_w \rightarrow C_6H_{6-w}[SiZ_{3-c}((CR^2R^3)_kCR^4R^5CR^6H(CR^8R^9)_hSi(OC_aH_{2a}R_f)_3)_c]_w$ (j) when X is a substituted cyclohexane of the type, as previously defined, which can be abbreviated $C_6H_{12-w}Y_w$, wherein w is the number of substituents; then:

Eqn. 10A:

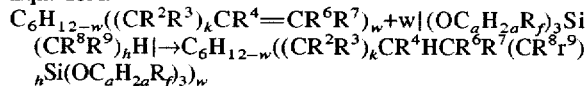

For convenience the reaction of Equations denoted A or B above is chosen depending upon the commercial availability of the starting reagents. In each set of equations where an A and B are presented, h=0 in Eqn. A and k=0 in Eqn. B. Specific sources of reactants are listed hereinafter just prior to the Examples. A transition metal catalyst such as platinum, or a free radical initiatior is employed in an effective amount. Examples of suitable free radical initators include "VAZO" azo compounds available from E. I. du Pont de Nemours and Company, Wilmngton, Del.

These reactions can be conducted at a temperature of from about 25° C. to about 100° C. Preferably the process is conducted at about 80° C. to about 100° C. The pressure employed is typically ambient, about 1 atm (1.01×10$^5$ Pa). The reactions are carried out under an inert gas atmosphere, although use of an air atmosphere is not precluded. Reaction time is typically from about 4 hours to about 24 hours.

Use of solvent is not required in these reactions. Suitable solvents which may be employed are those capable of dissolving the reactants, such as toluene or THF, and which do not interfere with the reaction or generate undesirable by-products. The desired product can be isolated by any means known to those skilled in the art. Preferably the desired product is isolated by removal of volatiles under reduced pressure.

NMR and mass spectrometry have been used to characterize product purities. Typically, yields of completed reacted material exceed 95%, with the prinicpal impurities being either reverse (Markovnikov) hydrosilyation or incompletely substituted material containing unreacted —CH=CH$_2$ groups.

The following show the preparation of compounds of formula I (k) (and IA(k) when replacing the group $Si(OC_aH_{2a}R_f)_3$ with $Si(R^{10})(OC_aH_{2a}R_f)_2$):

Eqn. 11A:
$CR^7R^6$=$CR^4(CR^3R^2)_k(CF_2)_v(CR^2R^3)_kCR^4$=$CR^6R^7$+HSi $(OC_aH_{2a}R_f)_3 \rightarrow (OC_aH_{2a}R_f)_3SiCR^7R^6CR^4H(CR^3R^2)_k$ $(CF_2)_v(CR^2R^3)_kCR^4HCR^6 R^7$—$Si(OC_aH_{2a}R_f)_3$ Synthesis of the compounds of formula I(k) (and IA(k) when replacing the group $Si(OC_aH_{2a}R_f)_3$ with $Si(R^{10})$ $(OC_aH_{2a}R_f)_2$) can also be realized by insertion of unsaturated trifluoroalkoxysilanes or trihalosilanes into the C—I bond of $I(CF_2)_vI$, followed by reduction of the C—I to C—H using standard organic reduction reagents, as shown below in Equation 11B. (P. Girard et al. in J. Am. Chem. Soc. (1980), vol 102, pp 2693–2698 describe the use of SmI$_2$ in reduction reactions.) Examples of suitable reagents are zinc metal, tri-n-butyl tin hydride or samarium iodide.

Eqn. 11B:
$I(CF_2)_vI+2CR^4R^5$=$CR^6(CR^8R^9)_hSi(OC_aH_{2a}R_f)_3 \rightarrow$ $(OC_aH_{2a}R_f)_3Si(CR^9R^8)_hCR^6ICR^5R^4(CF_2)_vCR^4R^5CR^6I$ $(CR^8R^9)_hSi(OC_aH_{2a}R_f)_3$ which can be converted to the following with, for example, samarium iodide (SmI$_2$), $(OC_aH_{2a}R_f)_3Si(CR^9R^8)_hCR^6HCR^5R^4(CF_2)_vCR^4R^5CR^6H$ $(CR^8R^9)_h(OC_aH_{2a}R_f)_3$.

Yields of the fluoroalkoxysilanes of formula I can be >99% using HSi(OCH$_2$CF$_3$)$_3$ and CH$_2$=CHSi(OCH$_2$CF$_3$)$_3$; slightly lower yields are found using HSi(OCH$_2$C$_3$F$_7$)$_3$ and CH$_2$=CHSi(OCH$_2$F$_7$)$_3$. This is believed to be due to the steric demands of the large tris(heptafluorobutoxy)silanes. Some branching is observed due to Markovnikov (α) addition of the silyl hydride.

Hydrosilylation of HSi(OR$^{10}$)$_3$, wherein R$^{10}$ is defined above, onto polycarbosilane precursors, for example (Si (CH$_2$CH$_2$CH$_2$Si(CH$_2$CH=CH$_2$)$_3$)$_4$, leads to the formation of the "dendrimer" compounds of formula II. The synthesis of the dendrimers of formula II can start with the exhaustive allylation of tetrachlorosilane with a 10% excess of allylmagnesium bromide in diethyl ether (reflux, 4 h) to produce tetrallylsilane. The allyl groups of tetraallylsilane are hydrosilylated at room temperature for about 1–2 days with either trichlorosilane, dichloromethylsilane or chlorodimethylsilane (25% excess in the presence of a platinum catalyst, 10$^{-4}$ to 10$^{-5}$ mol per double bond) and an optional solvent, such as toluene or THF, to give the first generation dendrimers of formula II containing Si—Cl functional groups. Next, all the Si—Cl groups are replaced by SiCH$_2$CH=CH$_2$ groups by reaction with an excess of allylmagnesium bromide in diethyl ether to produce dendrimers with 4 to 12 allyl end-groups. Hydrosilylation of these dendrimers by HSi(OCH$_2$CF$_3$)$_3$, HSi(OCH$_2$(CF$_2$) $_2$CF$_3$)$_3$ or HSi(OCH$_2$CH$_3$)$_3$ yields the dendrimers of formula II.

This route offers a unique flexibility; not only can the degree of branching be adjusted by replacing HSiCl$_3$ with HSiCl$_2$CH$_3$ or HSiCl(CH$_3$)$_2$ in the initial hydrosilylation, but also the length of the branches can be varied. With similar high yields, for example, vinyl-based silane dendrimers can be prepared up to the fourth generation by using vinylmagnesium chloride in tetrahydrofuran (THF) in the alkenylation step. (See U.S. Pat. No. 5,276,110 incorporated by reference herein.) As an additional benefit the reactive Si-Cl end groups allow an easy functionalization of the dendrimer surface to produce formula II compounds by direct reaction with alcohols or fluoroalcohols.

The compounds of formula ImI are prepared by dissolving a fluorine-bearing silane, such as one having the formula Si(OCH$_2$R$_f$)$_4$, wherein R$_f$ is as defined in formula III, or mixed silanes, such as Si(OCH$_2$R$_f$)$_x$(OR)$_{4-x}$, wherein R is C$_1$ to about C$_8$ alkyl, and x=1–3, in a solvent in which water is soluble, such as isopropyl alcohol (IPA). A soluble source of fluoride ion, such as CsF, is added to the solution along with less than a 1.5:1 molar excess of water. The solution is maintained, with optional heating, until the water has been substantially consumed. The byproduct alcohols and any unreacted water are then removed from the system by, for instance, distillation. The remaining material is an oligomeric silicate with sufficient residual fluorine-bearing groups to be soluble in fluorinated solvents.

Alternatively, polysilicates of formula Imi can be made by combining a fluorine-bearing silane such as Si(OCH$_2$C$_3$F$_7$)$_4$ (FBS) with a stoichiometric deficiency (i.e., <2:1) of trifluoroacetic acid (TFA) or other strong fluorocarboxylic acid. The solution will generally be heated so as to promote extensive reaction between the silane and acid. Reaction byproducts (ester, alcohol and any unreacted acid) are then removed, for example, by distillation.

Preparation of the oligomeric compounds of formula IV can proceed in similar fashion. In the alternative process using a strong fluorocarboxylic acid, heating is optional.

Formula III and formula IV are an idealized formulas which correspond to 100% crosslinking of the SiOH group; however, there can be residual uncrosslinked SiOH groups during preparation. z is the molar ratio of water or other gelling agent to silane. R$_f$ is preferably CF$_3$, C$_2$F$_5$ or C$_3$F$_7$ for formula III and C$_6$F$_{13}$, n-C$_8$F$_{17}$ and n-C$_{10}$F$_{21}$ for formula IV and a is preferably 1 or 2.

Using trifluoroacetic acid and fluorinated solvents, the fluorine-bearing compounds of formula I, IA, II, ImI and IV of the present invention can be condensed into silica networks using non-aqueous sol-gel techniques. For example, the condensation of $Si(OSi(CH_3)_2CH_2CH_2Si(OCH_2C_3F_7)_3$ by $CF_3COOH$ in perfluoro(butyl THF) (FC-75) produces a clear gel, demonstrating that inorganic hybrid networks can be easily formed in fluorinated solvents. The advantage of using these new fluoroalkoxysilanes is that they are soluble in fluorinated solvents, thus one can manage sol-gel condensation and form inorganic/organic network materials using dissolved fluoropolymers in perfluorinated solvents such as hexafluorbenzene and perfluoro(butyl-THF) using trifluoroacetic acid in lieu of more conventional gelling agents. These network materials can then be used to coat a substrate, such as glass, to form a film. The fluorine-bearing compounds of formula I, IA, III and IV (and those of formula II that are soluble in fluorinated solvents) of the present invention can be also used in conjunction with dissolved fluoropolymers to provide semi-interpenetrating networks useful for a variety of applications including as primers for adhesion.

The compounds of formula II are useful in abrasion resistant materials, impact resistant glasses, and can act as crosslinking agents for some functionalized organic polymers.

EXAMPLES

All reactions were carried out in a Vacuum Atmospheres Co. dry box or under nitrogen. In the examples, all commercial reagents were distilled prior to use. Trichlorosilane, tetravinylsilane, tetrachlorosilane, vinyltrichlorosilane, allyltrichlorosilane, 1,3,5,7-tetramethylcyclotetra-siloxane, tetrakis(dimethylsiloxy)-silane, 1,1,3,3-tetramethyldisiloxane, and 1,3,5,7,9-pentamethylcyclopentasiloxane were purchased from Aldrich Chemical Co., Milwaukee, Wis., Huls America Inc., Piscataway, N.J. or PCR Inc. Gainesville, Fla. Trifluoroethanol and n-heptafluorobutanol were obtained from PCR Inc. $Si(OCH_2CF_3)_4$, $Si(OCH_2(CF_2)CF_3)_4$, $HSi(OCH_2CF_3)_3$, $CH_2=CHSi(OCH_2CF_3)_3$, $Si(CH_2CH_2CH_2Si(CH_3)_2CH_2CH=CH_2)_4$, $Si(CH_2CH_2CH_2SiCH_3(CH_2CH=CH_2)_2)_4$, and $Si(CH_2CH_2CH_2Si(CH_2CH=CH_2)_3)_4$ were synthesized by slight modifications of published procedures. Platinum divinylsiloxane complex (3–3.5% Pt concentration in xylene, Huls $PC_{072}$) was obtained from Huls America Inc. and diluted 5:1 by volume (toluene, Pt complex) prior to use. Toluene and tetrahydrofuran was reagent grade and purified by distillation from calcium hydride prior to use. Tetraallylsilane was synthesized by a modification of a published procedure (J. Organomet. Chem., 84 (1975), pp 199–229). Vinylpolyfluoroalkanes were prepared from $I(CF_2)_6I$ available from PCR Inc. "FLUORINERT" FC-75 and "FLUORINERT" FC-40 solvents were obtained from PCR Inc. Hexafluorobenzene was obtained from Aldrich Chemical, Inc. The mass spectroscopy experiments were performed on a Finnigan 4615B GC/MS quadrupole mass spectrometer (San Jose, Calif.). An electron impact source configuration operating at 200° C. and a source pressure of $1.0 \times 10^{-6}$ Torr was used. The mass spectrometer was scanned at a rate of about 1000 Daltons/second. All mass spectral peaks were recorded as sum of the ion plus potassium (M+39). Proton and carbon NMR were determiined on a GE model QE-300 instrument. Elemental analyses were performed by Oneida Research Services Inc., One Halsey Road, Whitesboro, N.Y.

The following are abbreviations used in the description and the examples:

Et—ethyl
FBS=tetra(heptafluorobutoxy)silane, $Si(OCH_2C_3F_7)_4$
FC-75=perfluoro(butyl THF)
FES=tetra(trifluoroethoxy)silane, $Si(OCH_2CF_3)_4$
HFB=hexafluorobenzene, $C_6F_6$
HFBS=tri(heptafluorobutoxy)silane, $HSi(OCH_2C_3F_7)_3$
Me=methyl, $CH_3$
PP-11=perfluoro phenanthrene
TEOS=tetraethoxysilane, $Si(OCH_2CH_3)_4$
TFA=trifluoroacetic acid, $CF_3COOH$
THF=tetrahydrofuran

Example 1

Synthesis of $Si(CH_2CH_2Si(OCH_2CF_3)_3)_4$

A mixture of 2.39 g (7.34 mmol) of $HSi(OCH_2CF_3)_3$, 2 drops of Pt catalyst and 0.255 g (1.87 mmol) of tetravinylsilane was heated to 90° C. for 6 hr. After cooling, the residual silane was removed in vacuo leaving a brownish oil which was identified as $Si(CH_2CH_2Si(OCH_2CF_3)_3)_4$. MS (m/3) 1480 (M +39, 100%), 1153 (($H_2C=CH)Si(CH_2CH_2Si(OCH_2CF_3)_3)_3+39$, 20%). $^{13}C$ NMR($C_6D_6$) 1.31, 1.86, 2.31, 2.53 ($SiCH_2$), 61.8 (q, $CH_2CF_3$, $^2J(CF)$=36.6 Hz), 124.53 (q, $CF_3$, $^1J(CF)$=277.9 Hz). Small amounts of —$SiCH(CH_3)Si(OCH_2CF_3)_3$ groups due to Markovnikov addition (−0.55, 7.79 ppm) were observed.

Example 2

Synthesis of $Si(CH_2CH_2Si(OCH_2(CF_9)_2CF_3)_3)_4$

The reaction was performed in a manner similar to Example 1 using 0.250 g (1.83 mmol) of tetravinylsilane and 4.597 g (7.34 mmol) of $HSi(OCH_2(CF_2)_2CF_3)_3$. Workup yielded $Si(CH_2CH_2Si(OCH_2(CF_2)_2CF_3)_3)_4$ as a brownish oil. $^{13}C$ NMR(THF-$d_8$)1.47, 2.06, 2.32, 2.64 ($SiCH_2$), 61.5 (t, $CH_2CF_2$, $^2J(CF)$=27.2 Hz), 110–120 (M, $(CF_2)_2CF_3$). Small amounts of—$SiCH(CH_3)Si(OCH_2(CF_2)_2CF_3)_3$ groups due to Markovnikov addition (−0.4, 7.87 ppm) were observed.

Example 3

Synthesis of $Si(OSi(CH_3)_2CH_2CH_2Si(OCH_2CF_3)_3)_4$

A solution consisting of 0.497 g (1.51 mmol) of $Si(OSi(CH_3)_2H)_4$, 2.149 g (6.10 mmol) of $CH_2=CHSi(OCH_2CF_3)_3$ and two drops of Pt catalyst was heated to 90° C. for 6 hr. After cooling, the solution was stirred an additional 16 hr at room temperature. Removal of all volatiles in vacuo gave the product, $Si(OSi(CH_3)_2CH_2CH_2Si(OCH_2CF_3)_3)_4$, in quantitative yield. Small amounts of —$SiCH(CH_3)Si(OCH_2CF_3)_3$ groups due to Markovnikov addition were also observed by NMR. $^{13}C$ NMR($C_6D_6$) −0.636, −0.603 (major isomer, $CH_3Si$), 1.47 (minor isomer, $CH_3Si$), 2.10 ($SiCH_2$), 7.37 (SiCH), 7.40 ($CH_3CH$), 9.03 ($SiCH_2$), 62.14 (q (major), $CH_2CF_3$, $^2J(CF)$=36.5 Hz), 62.21 (q (minor), $CH_2CF_3$, $^2J(CF)$=36.5 Hz), 125.16 (q, $CF_3$, $^1J(CF)$=277.7 Hz). MS (m/e) 1736 (M+39, 100%)

Example 4

Synthesis of $Si(OSi(CH_3)_2CH_2CH_2Si(OCH_2(CF_2)_2CF_3)_3)_4$

The reaction was performed in a manner similar to Example 3 using 10.049 g (15.4 mmol) of $CH_2=CHSi$ (OCH$_2$(CF$_2$)$_2$CF$_3$)$_3$, 1.241 g (3.78 mmol) of Si(OSi(CH$_3$)$_2$H)$_4$, and three drops of Pt catalyst in 10 ml of toluene. Workup yielded 9.95 g (90%) of Si(OSi(CH$_3$)$_2$CH$_2$CH$_2$Si(OCH$_2$(CF$_2$)$_2$CF$_3$)$_3$)$_4$ as the sole product. $^{13}$C NMR(THF-d$_8$)−0.797, −0.753 (major isomer, CH$_3$Si), 1.03, 1.40, 1.48 (minor isomer, CH$_3$Si), 2.04 (SiCH$_2$), 6.62 (SiCH), 7.30 (CH$_3$CH), 8.89, 8.93 (SiCH$_2$), 61.61 (t, CH$_2$CF$_3$, $^2$J(CF)=27.6 Hz), 105–120 (m, CF$_3$(CF$_2$)$_2$). MS (m/e) 2975 (M+39).

Example 5

Synthesis of Si(OSi(CH$_3$)$_2$CH$_2$CH$_2$CH$_2$Si(OCH$_2$CF$_3$)$_3$)$_4$

A mixture consisting of 3.003 g (8.20 mmol) of CH$_2$=CHCH$_2$Si(OCH$_2$CF$_3$)$_3$, 0.672 g (2.04 mmol) of Si(OSi(CH$_3$)$_2$H)$_4$ and one drop of Pt catalyst was heated to 90° C. for 4 hrs, then cooled and stirred at room temperature for 16 hr. The volatiles were removed in vacuo leaving 3.44 g (94%) of a yellow tinted liquid identified as Si(OSi(CH$_3$)$_2$CH$_2$CH$_2$CH$_2$Si(OCH$_2$CF$_3$)$_3$)$_4$. $^1$H NMR (C$_6$D$_6$) 0.26 (s, 6H), 0.72 (m, 4H), 1.61 (m, 2H), 3.71 (q, 6H). $^{13}$C NMR (C$_6$D$_6$) −0.53, −0.12 (s, SiCH$_3$), 14.07, 16.78, 16.81 (SiCH$_2$), 61.53 (q, CH$_2$CF$_3$, $^2$J(CF)=36.5 Hz). A small amount of Markovnikov addition product was also observed by NMR.

Example 6

Synthesis of cyclo-((CH)(CF$_3$CH$_2$O)$_3$SiCH$_2$CH$_2$CH$_2$)SiO$_4$)

A mixture consisting of 3.595 g (9.82 mmol) of cyclo-CH$_2$=CHCH$_2$Si(OCH$_2$CF$_3$)$_3$, 0.525 g (2.18 mmol) of ((CH$_3$)(H)SiO)$_4$ and one drop of Pt catalyst was heated to 90° C. for 4 hrs, then cooled and stirred at room temperature for 16 hr. The volatiles were removed in vacuo leaving 3.94 g of a brown-tinted liquid identified as cyclo-((CH$_3$)(CF$_3$CH$_2$O)$_3$SiCH$_2$CH$_2$CH$_2$)SiO)$_4$. $^1$H NMR (C$_6$D$_6$) 0.30 (m, 6H), 0.75 (m, 4H), 1.62 (m, 2H), 3.60 (q, 6H). $^{13}$C NMR (C$_6$D$_6$)−1.12 (s, SiCH$_3$), 13.67, 16.58, 21.41 (SiCH$_2$), 61.52 (q, CH$_2$CF$_3$, $^2$J(CF)=36.3 Hz). Some minor peaks were observed in the $^{13}$C NMR due to Markovnikov addition products.

Example 7

Synthesis of cyclo-((CH$_3$)(CF$_3$CH$_2$O)$_3$SiCH$_2$CH$_2$CH$_2$)SiO)$_5$)

A mixture consisting of 3.003 g (8.20 mmol) of CH$_2$=CHCH$_2$Si(OCH$_2$CF$_3$)$_3$, 0.493 g (1.64 mmol) of cyclo-((CH$_3$)(H)SiO)$_5$ and one drop of Pt catalyst was heated to 90° C. for 4 hrs, then cooled and stirred at room temperature for 16 hr. The volatiles were removed in vacuo leaving 3.11 g (89%) of a thick yellow-tinted liquid identified as cyclo-((CH$_3$)(CF$_3$CH$_2$O)$_3$SiCH$_2$CH$_2$CH$_2$)SiO)$_5$. $^1$H NMR (THF-d$_8$) 0.18 (s, 3H), 0.68 (m, 2H), 0.90 (m, 2H), 1.59 (m, 2H), 4.22 (q, 6H). A small amount of Markovnikov addition product was also observed by NMR.

Example 8

Synthesis of cyclo-((CH$_3$)((CF$_3$CH$_2$O)$_3$SiCH$_2$CH$_2$)SiO)$_4$

The reaction was performed in a similar manner to Example 3 using 0.525 g (1.53 mmol) of cyclo-((CH$_3$)(CH$_2$=CH)SiO)$_4$, 2.00 g (6.22 mmol) of HSi(OCH$_2$CF$_3$)$_3$ and two drops of Pt catalyst. Workup yielded ((CH$_3$)((CF$_3$CH$_2$O)$_3$SiCH$_2$CH$_2$)SiO)$_4$ as an oil. Some trisubstituted product was observed in the mass spectrum. $^{13}$C NMR (C$_6$D$_6$)−1.38, 1.29 (s, CH$_3$Si), 1.90 (SiCH$_2$), 7.95 (SiCH$_2$), 62.14 (q (major), CH$_2$CF$_3$, $^2$J(CF)=36.5 Hz), 61.83 (q (minor), CH$_2$CF$_3$, 2J(CF)=36.6 Hz), 124.53 (q, CF$_3$, $^1$J(CF)=278.0 Hz). MS (m/e) 1687 (M+39, 100%), 1361 (trisubstituted product +39, 12%).

Example 9

Synthesis of cyclo-((CH$_3$)(CF$_3$(CF$_2$)$_2$CH$_2$O)$_3$SiCH$_2$CH$_2$)SiO$_4$)

This reaction was performed in a manner similar to that in Example 3 using 0.500 g (1.45 mmol) of cyclo-((CH$_3$)(CH$_2$=CH)SiO)$_4$, 3.64 g (5.81 mmol) of HSi(OCH$_2$(CF$_2$)$_2$CF$_3$)$_3$ and two drops of Pt catalyst. Workup yielded ((CH$_3$)((CF$_3$(CF$_2$)$_2$CH$_2$O)$_3$SiCH$_2$CH$_2$)SiO)$_4$ as an oil. Some trisubstituted product (4–5%) was observed by NMR. $^{13}$C NMR(THF-d$_8$)−1.70, −1.65 (s, CH$_3$Si), 1.75 (SiCH$_2$), 7.80, 7.88 (SiCH$_2$), 61.55 (t, CH$_2$CF$_3$, $^2$J(CF)=27.6 Hz), 105–120 (m, CF$_3$(CF$_2$)$_2$).

Example 10

Synthesis of (CF$_3$CH$_2$O)$_3$SiCH$_2$CH$_2$(CF$_2$)$_6$CH$_2$CH$_2$Si(OCH$_2$CF$_3$)$_3$ This preparation was done in a manner similar to Example 3 using 0.258 g (0.782 mmol) of (CH$_2$=CH(CF$_2$)$_3$)$_2$, 0.526 g (1.61 mmol) of HSi(OCH$_2$CF$_3$)$_3$ and two drops of Pt catalyst. Workup yielded ((CF$_3$CH$_2$O)$_3$SiCH$_2$CH$_2$(CF$_2$)$_3$)$_2$ as the sole product by NMR. $^1$H NMR(C$_6$D$_6$) 0.68–0.79, 2.0–2.1 (m, AA'BB' pattern, SiCH$_2$CH$_2$Si), 3.51 (q, CH$_2$CF$_3$). $^{13}$C NMR(C$_6$D$_6$) 0.685 (s, CH$_2$Si), 25.03 (t, CH$_2$CF$_2$), 61.74 (q, CH$_2$CF$_3$, 2J(CF)=34.8 Hz), 105–120 (m, (CF$_2$)$_6$), 124.28 (q, CF$_3$, $^1$J(CF)=277.9 Hz). MS (m/e) 1045 (M+39, 100%).

Example 11

Synthesis of (CF$_3$(CF$_2$)$_2$CH$_2$O)$_3$SiCH$_2$CH$_2$(CF$_2$)$_6$CH$_2$CH$_2$Si(OCH$_2$(CF$_2$)$_2$CF$_3$)$_3$ This preparation was done in a manner similar to Example 3 using 0.252 g (0.713 mmol) of CH$_2$=CH(CF$_2$)$_6$CH=CH$_2$, 0.998 g (1.59 mmol) of HSi(OCH$_2$(CF$_2$)$_2$CF$_3$)$_3$ and three drops of Pt catalyst. The mixture was heated to 120° C. for 12 hr. Workup yielded (CF$_3$(CF$_2$)$_2$CH$_2$O)$_3$SiCH$_2$CH$_2$(CF$_2$)$_6$CH$_2$CH$_2$Si(OCH$_2$(CF$_2$)$_2$CF$_3$)$_3$ as the sole product by NMR. $^1$H NMR (THF-d$_8$) 1.1–1.3, 2.18–2.4 (m, AA'BB' pattern, SiCH$_2$CH$_2$Si), 4.48 (t, CH$_2$CF$_2$). $^{13}$C NMR (THF-d$_8$) 0.678 (s, CH$_2$Si), 61.64 (t, OCH$_2$CF$_2$, $^2$J(CF)=27.8 Hz), 105–120 (m, CF$_2$, CF$_3$), resonance for CH$_2$CF$_2$ is about 25 ppm and is obscured by solvent. MS (m/e) 1645 (M+39, 100%), 1019 (monosubstituted product +39,2%).

Example 12

Synthesis of (CF$_3$CH$_2$O)$_3$Si(CH$_2$)$_6$(CF$_2$)$_6$(CH$_2$)$_6$Si(OCH$_2$CF$_3$)$_3$ A mixture consisting of 2.002 g (4.29 mmol) of (CH$_2$=CH(CH$_2$)$_4$(CF$_2$)$_3$)$_2$, 2.82 g (8.64 mmol) of HSi(OCH$_2$CF$_3$)$_3$ and 10 microliters of Pt catalyst was heated to 90° C. for 4 hr, cooled and stirred for 16 h. The excess silane was removed in vacuo yielding 3.98 g (83%) of a thick liquid identified as (CF$_3$CH$_2$O)$_3$Si(CH$_2$)$_6$(CF$_2$)$_6$(CH$_2$)$_6$Si(OCH$_2$CF$_3$)$_3$. $^1$H NMR (C$_6$D$_6$) 0.42 (m, SiCH$_2$), 0.82–1.09 (m, CH$_2$CH$_2$), 1.20 (m, CH$_2$), 1.38 (m, CH$_2$), 1.62–1.90 (m, $CH_2CF_2$), 3.59 (q, $CH_2CF_3$). $^{13}C$ NMR ($C_6D_6$) 9.66 ($CH_2Si$), 20.59, 22.19 28.89 ($CH_2$), 31.0 (t, $CH_2CF_2$), 32.6 ($CH_2$), 61.54 (q, $CH_2CF_3$, $^2J(CF)=36.5$ (q, $CF_3$).

Example 13

Synthesis of $(CF_3(CF_2)_2CH_2O)_3Si(CH_2)_6(CF_2)_6(CH_2)_6Si(OCH_2(CF_2)_2CF_3)_3$ A mixture consisting of 1.254 g (2.69 mmol) of $(CH_2=CH(CH_2)_4(CF_2)_3)_2$, 3.37 g (5.38 mmol) of $HSi(OCH_2(CF_2)_2CF_3)_3$ and 10 microliters of Pt catalyst was heated to 90° C. for 4 hr, cooled and stirred for 16 h. The excess silane was removed in vacuo yielding 3.69 g (97%) of a thick, colorless liquid identified as $(CF_3(CF_2)_2CH_2O)_3Si(CH_2)_6(CF_2)_6(CH_2)_6Si(OCH_2(CF_2)_2CF_3)_3$. $^1H$ NMR (THF-$d_8$) 0.90 (m, $SiCH_2$), 1.40 (m, $CH_2$), 1.40-1.68 (m, $(CH_2)_3$), 2.03-2.23 (m, $CH_2CF_2$), 4.40 (t, $CH_2CF_2$). $^{13}C$ NMR($C_6D6$) 9.73 ($CH_2Si$), 21.04, 22.63, 29.49 ($CH_2$), 31.66 (t, $CH_2CF_2$), 33.22 ($CH_2$), 61.35 (t, $CH_2CF_3$, $^2J(CF)=24.7$ Hz), 107-120 (q, $CF_2$ resonances).

Example 14

Synthesis of $Si(CH_2CH_2CH_2Si(CH_3)CH_2CH_2CH_2Si(OCH_2CH_3)_3)_4$

Triethoxysilane (5.567 g, 0.034 mol) was added to 5.023 g (8.47 mmol) of $Si(CH_2CH_2CH_2Si(CH_3)_2CH_2CH=CH_2)_4$ and 50 microliters of Pt catalyst and heated to reflux for 5 hr. After cooling, an additional 2.796 g (0.0017 mol) of triethoxysilane and one drop of Pt catalyst solution was added, and the solution was refluxed an additional 8 hr and cooled. The excess triethoxysilane was removed in vacuo leaving 7.78 g (74%) of a tea colored liquid identified as $Si(CH_2CH_2CH_2Si(CH_3)_2CH_2CH_2CH_2Si(OCH_2CH_3)_3)_4$. Approximately 20% of product due to Markovnikov addition were observed. $^1H$ NMR($C_6D_6$) -0.01 (s, $SiCH_3$), 0.19 (s, $SiCH_3$ Markovnikov product), 0.58-0.86 (m, $CH_2$), 1.15 (t, $OCH_2$), 1.4-1.8 (m, $CH_2$), 3.76 (q, $CH_3$). $^{13}C$ NMR ($C_6D_6$) -2.59 ($SiCH_3$), -2.17 ($SiCH_3$, Markovnikov product), 16.14, 18.52, 19.62, 20.40, 21.21 ($CH_2$), 19.08 ($CH_3$), 58.7 ($OCH_2$).

Example 15

Synthesis of $Si(CH, CH_2CH_2Si(CH_3)_2CH_2CH_2CH_2Si(OCH_2CF_3)_3)_4$

To a mixture containing 1.998 g (3.37 mmol) of $Si(CH_2CH_2CH_2Si(CH_3)_2CH_2CH=CH_2)_4$ and 30 microliters of Pt catalyst solution was added 6.602 g (0.020 mol) of $HSi(OCH_2CF_3)_3$ dropwise over a period of 0.5 hr. After the addition, the mixture was heated to 90° C. for 6 hr and stirred at room temperature for 16 hr. After removing the excess silane in vacuo, and filtering through activated charcoal, 57.4 g (90%) of $Si(CH_2CH_2CH_2Si(CH_3)_2CH_2CH_2CH_2Si(OCH_2CF_3)_3)_4$ was obtained as a thick tea-colored liquid. $^1H$ NMR($C_6D_6$) 0.08 (s, $SiCH_3$), 0.51-0.84 (m, $CH_2$), 1.40-1.62 (m, $CH_2$), 3.70 (q, $CH_2CF_3$). $^{13}C$ NMR($C_6D_6$) -3.04 ($SiCH_3$), 14.24, 17.11, 18.50, 19.55, 19.93, 20.98 ($CH_2$), 61.52 ($CH_2CF_3$, $^2J(CF)=36.6$ Hz), 124.5 ($CF_3$, $^1J(CF)=278$ Hz).

Example 16

Synthesis of $Si(CH_2CH_2CH_2SiCH_3(CH_2CH_2CH_2Si(OCH_2CH_3)_3)_2)_4$

A mixture containing 5.011 g (7.18 mmol) of $Si(CH_2CH_2CH_2SiCH_3(CH_2CH=CH_2)_2)_4$, 7.035 g (0.043 mol) of triethoxysilane and 30 microliters of Pt catalyst solution was heated to reflux for 5 hr. After checking by NMR, an additional 2.364 g (0.014 mol) of triethoxysilane and 1 drop of Pt catalyst solution were added, and the resulting mixture was refluxed for 8 hr. After cooling and removing the excess silane in vacuo, 10.74 g (74%) of $Si(CH_2CH_2CH_2SiCH_3(CH_2CH_2CH_2Si(OCH_2CH_3)_3)_2)_4$ was obtained as a tea-colored liquid. Aproximately 20% of product due to Markovnikov addition were observed. $^1H$ NMR ($C_6D_6$) -0.02 (s, $SiCH_3$), 0.08 (s, $SiCH_3$) Markovnikov product) 0.58-0.82 (m, $CH_2$), 1.13 (t, $CH_3$), 1.38-1.80 (m, $CH_2$), 3.77 (q, $CH_2CH_3$). $^{13}C$ NMR($C_6D_6$) -4.40 ($SiCH_3$), -4.14 ($SiCH_3$ Markovnikov), 16.25, 18.57, 18.70, 18.78, 19.62, 20.33 ($CH_2$), 19.07 ($CH_3$), 59.78 ($OCH_2$).

Example 17

Synthesis of $Si(CH_2CH_2CH_2SiCH_3(CH_2CH_2CH_2Si(OCH_2CF_3)_3)_2)_4$

To a mixture containing 1.515 g (2.17 mmol) of $Si(CH_2CH_2CH_2SiCH_3(CH_2CH=CH_2)_2)_4$ and six drops of Pt catalyst solution dissolved in 20 ml of toluene was added 7.098 g (0.022 mol) of $HSi(OCH_2CF_3)_3$ dropwise over a period of 0.5 hr. After the addition, the mixture was heated to 100° C. for 8 hr. After cooling, NMR showed the reaction to be incomplete and an additional 0.718 g (2.2 mmol) of $HSi(OCH_2CF_3)_3$ and 1 drop of Pt catalyst were added. This mixture was heated to 110° C. for 6 hr and stirred at room temperature for 64 hr. After removing the excess silane in vacuo, 5.23 g (73%) of $Si(CH_2CH_2CH_2SiCH_3(CH_2CH_2CH_2Si(OCH_2CF_3)_3)_2)_4$ was obtained as a thick orange-tinted liquid. $^{13}C$ NMR($C_6D_6$) -5.07 ($SiCH_3$), 14.35, 17.48, 18.42, 19.50, 19.62, 23.08 ($CH_2$), 61.90 ($CH_2CF_3$, $^2J(CF)=36.7$ Hz), 124.6 ($CF_3$, $^1J(CF)=278$ Hz).

Example 18

Synthesis of $Si(CH_2 CH_2CH_2Si(CH_2CH_2CH_2Si(OCH_2CF_3)_3)_3)_4$

A mixture containing 1.853 g (2.31 mmol) of $Si(CH_2CH_2CH_2Si(CH_2CH=CH_2)_3)_4$, 12.091 g (37.07 mmol) of $HSi(OCH_2CF_3)_3$, and 10 drops of Pt catalyst solution in 10 ml of toluene was heated to reflux for 6 hr followed by stirring at room temperature for 90 hr. The mixture was heated an additional 4 hr and cooled. After removing the excess silane in vacuo, 7.92 g (73%) of $Si(CH_2CH_2CH_2Si(CH_2CH_2CH_2Si(OCH_2CF_3)_3)_3)_4$ was obtain as a thick orange-tinted liquid. $^1H$ NMR (toluene-$d_8$) 0.59-1.00 (m, $CH_2$), 1.40-1.75 (m, $CH_2$), 3.82 (broad q, $CH_2CF_3$). $^{13}C$ NMR($C_6D_6$) 14.08, 16.53, 17.18, 18.0, 18.5, ($CH_2$, remaining line obscured by toluene), 61.30 ($CH_2CF_3$, $^2J(CF)=36.6$ Hz), 124.2 ($CF_3$, $^1J(CF)=278$ Hz).

Example 19

Preparation of Polysilicates from FBS

FBS/2-propanol/deionized water/0.5% CsF in 2-propanol were combined with mixing in the sequence given at the following levels by weight, 82.2%/14.2%/2.4%/1.2%. The final solution contained a water/FBS molar ratio of 1.33 and 6.07 wt. % solids. This solution was heated slowly for two hours until volatile products could be removed by distillation. After 30 min. of distillation, the flask was allowed to cool and the contents analyzed by gas chromatography. The analysis indicated that water had essentially completely reacted. The cooled material was allowed to evaporate at room temperature until it had lost 35% of its original weight.

The concentrated material was used to make up solutions in hexafluorobenzene (8.6%) and in FC-75 (8.9%). Both were very homogeneous and formed clear films when flow or dip coated on glass slides.

Silicon-29 NMR was run on the concentrate and indicated substantial reaction of the starting material (ca. 90%) to form a broad range of polysilicates with Q1 through Q4 structures (Si atom has 1 to 4 bonds to other Si atoms through oxygen). (Many of the species must contain residual fluorine-bearing groups in order for the solubility in fluorinated solvents to be observed.)

What is claimed is:

1. A compound having the formula $$X(Si(Oc_aH_{2a}R_f)_3)_n \qquad I$$

wherein:

X is at least one organic link selected from the group consisting of:
(a) $R^1_m SiY_{4-m}$;
(b) ring structures

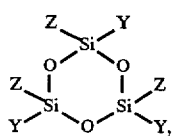
Ib(i)

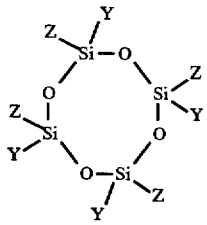
Ib(ii)

and

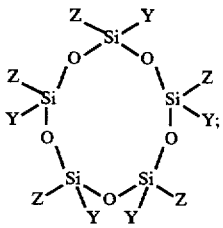
Ib(iii)

(c) $R^1_m Si(OSi(CH_3)_2Y)_{4-m}$;
(d) $CH_3 SiY_2 OSiY_2 CH_3$;
(e) $Y_3 SiOSiY_3$;
(f) $Y_2(CH_3)Si(CH_2)_b Si(CH_3)Y_2$;
(g) $Y_3 Si(CH_2)_b SiY_3$;
(h) $Y_3 SiC_6 H_4 SiY_3$;
(i) substituted benzene, including all isomers, selected from the group consisting of:
 (i) $C_6 H_3(SiZ_{3-c}Y_c)_3$;
 (ii) $C_6 H_2(SiZ_{3-c}Y_c)_4$;
 (iii) $C_6 H(SiZ_{3-c}Y_c)_5$; and
 (iv) $C_6(SiZ_{3-c}Y_c)_6$; and
(j) substituted cyclohexane, including all stereoisomers, selected from the group consisting of:
 (i) $1,2\text{-}C_6 H_{10}(Y)_2$; $1,3\text{-}C_6 H_{10}(Y)_2$; $1,4\text{-}C_6 H_{10}(Y)_2$;
 (ii) $1,2,4\text{-}C_6 H_9(Y)_3$; $1,2,3\text{-}C_6 H_9(Y)_3$; $1,3,5\text{-}C_6 H_9(Y)_3$;
 (iii) $1,2,3,4\text{-}C_6 H_8(Y)_4$; $1,2,4,5\text{-}C_6 H_8(Y)_4$; $1,2,3,5\text{-}C_6 H_8(Y)_4$;
 (iv) $1,2,3,4,5\text{-}C_6 H_7(Y)_5$; and
 (v) $C_6 H_6(Y)_6$;
(k) $Y(CF_2)_v Y$ $R_f$ has up to about 18 carbon atoms and is selected from the group consisting of:
(a) $C_1$ to about $C_{18}$ perfluoroalkyl;
(b) $-[CF_2 CF(CF_3)O]_r- CF_2- CF_2- CF_3$, wherein r is an integer of at least 1;
(c) $-CF_2-(CF_2-O)_q-CF_3$, wherein q is an integer of at least 2; and
(d) $-CH_2-C(CF_3)_2-CF_2-CF_2-CF_3$;

wherein up to 50% of the fluorine of the $R_f$ group is optionally substituted with hydrogen;

a is an integer from 1 to about 10;

b is an integer from 1 to about 10;

c is 1, 2 or 3;

m is 0, 1 or 2;

n is an integer greater than or equal to 2;

v is an even integer from 2 to about 14;

$R^1$ is $C_1$ to about $C_8$ alkyl or aryl;

Y is $-(CR^2 R^3)_k CR^4 R^5 CR^6 R^7 (CR^8 R^9)_h-$ $R^2$ to $R^9$ are each independently hydrogen, $C_1$ to about $C_8$ alkyl, or aryl, provided that at least one of $R^4$ to $R^7$ is hydrogen;

k and h are each independently an integer from 0 to 10, provided that at least one of k or h is zero;

Z is $C_1$ to about $C_4$ alkyl, 3,3,3-trifluoropropyl, aralkyl or aryl.

2. The compound of claim 1 wherein X is selected from the group consisting of: $R^1_m SiY_{4-m}$;

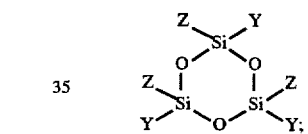
Ib(i)

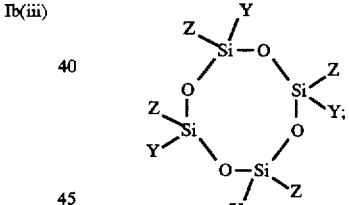
Ib(ii)

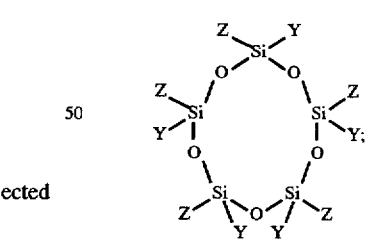
Ib(iii)

$R^1_m Si(OSi(CH_3)_2Y)_{4-m}$ and $Y(CF_2)_v Y$; and $R_f$ is $CF_3$, $C_2 F_5$ or $C_3 F_7$.

3. The compound of claim 2 selected from the group consisting of:

$Si(CH_2 CH_2 Si(OCH_2 CF_3)_3)_4$;
$Si(CH_2 CH_2 Si(OCH_2 CF_2 CF_3)_3)_4$;
$Si(CH_2 CH_2 Si(OCH_2(CF_2)_2 CF_3)_3)_4$;
$Si(OSi(CH_3)_2 CH_2 CH_2 Si(OCH_2 CF_3)_3)_4$;
$Si(OSi(CH_3)_2 CH_2 CH_2 Si(OCH_2(CF_2)_2 CF_3)_3)_4$;
$Si(OSi(CH_3)_2 CH_2 CH_2 CH_2 Si(OCH_2 CF_3)_3)_4$;
cyclo-$((CH_3)(CF_3 CH_2 O)_3 SiCH_2 CH_2)SiO)_4$;

cyclo-((CH$_3$)(CF$_3$CH$_2$O)$_3$SiCH$_2$CH$_2$CH$_2$)SiO)$_4$;
cyclo-((CH$_3$)(CF$_3$CH$_2$O)$_3$SiCH$_2$CH$_2$CH$_2$)SiO)$_5$;
cyclo-((CH$_3$)(CF$_3$(CF$_2$)$_2$CH$_2$O)$_3$SiCH$_2$CH$_2$)SiO)$_4$;
(CF$_3$CH$_2$O)$_3$SiCH$_2$CH$_2$(CF$_2$)$_6$CH$_2$CH$_2$Si(OCH$_2$CF$_3$)$_3$;
(CF$_3$(CF$_2$)$_2$CH$_2$O )$_3$SiCH$_2$CH$_2$(CF$_2$)$_6$CH$_2$CH$_2$Si(OCH$_2$(CF$_2$)$_2$CF$_3$)$_3$; and
(CF$_3$CH$_2$O)$_3$Si(CH$_2$)$_6$(CF$_2$)$_6$(CH$_2$)$_6$Si(OCH$_2$CF$_3$)$_3$.

4. A compound having the formula $$X(R^{10}Si(OC_aH_{2a}R_f)_2)_n \quad \text{IA}$$

wherein:

X is at least one organic link selected from the group consisting of:
(a) R$^1_m$SiY$_{4-m}$;
(b) ring structures

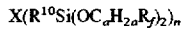 IA (b) (i)

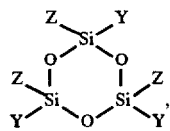 IA (b) (ii)

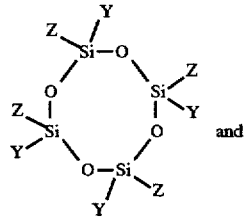 and

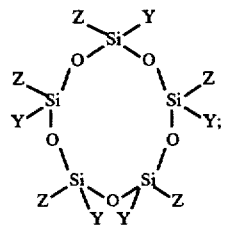 IA (b) (iii)

(c) R$^1_m$Si(OSi(CH$_3$)$_2$Y)$_{4-m}$;
(d) CH$_3$SiY$_2$OSiY$_2$CH$_3$;
(e) Y$_3$SiOSiY$_3$;
(f) Y$_2$(CH$_3$)Si(CH$_2$)$_b$Si(CH$_3$)Y$_2$;
(g) Y$_3$Si(CH$_2$)$_b$SiY$_3$;
(h) Y$_3$SiC$_6$H$_4$SiY$_3$;
(i) substituted benzene, including all isomers, selected from the group consisting of:
  (i) C$_6$H$_3$(SiZ$_{3-c}$Y$_c$)$_3$;
  (ii) C$_6$H$_2$(SiZ$_{3-c}$Y$_c$)$_4$;
  (iii) C$_6$H(SiZ$_{3-c}$Y$_c$)$_5$; and
  (iv) C$_6$(SiZ$_{3-c}$Y$_c$)$_6$; and
(j) substituted cyclohexane, including all stereoisomers, selected from the group consisting of:
  (i) 1,2-C$_6$H$_{10}$(Y)$_2$; 1,3-C$_6$H$_{10}$(Y)$_2$; 1,4-C$_6$H$_{10}$(Y)$_2$;
  (ii) 1,2,4-C$_6$H$_9$(Y)$_3$; 1,2,3-C$_6$H$_9$(Y)$_3$; 1,3,5-C$_6$H$_9$(Y)$_3$;
  (iii) 1,2,3,4-C$_6$H$_8$(Y)$_4$; 1,2,4,5-C$_6$H$_8$(Y)$_4$; 1,2,3,5-C$_6$H$_9$(Y)$_4$;
  (iv) 1,2,3,4,5-C$_6$H$_7$(Y)$_5$; and
  (v) C$_6$H$_6$(Y)$_6$;

R$_f$ has up to about 18 carbon atoms and is selected from the group consisting of:
(a) C$_1$ to about C$_{18}$ perfluoroalkyl;
(b) —[CF$_2$CF(CF$_3$)O]$_r$—CF$_2$—CF$_2$—CF$_3$, wherein r is an integer of at least 1;
(c) —CF$_2$(CF$_2$O)$_q$—CF$_3$, wherein q is an integer of at least 2; and
(d) —CH$_2$—C(CF$_3$)$_2$—CF$_2$—CF$_2$—CF$_3$;
each R$_f$ optionally substituted with one or more hydrogen;

Z is C$_1$ to about C$_4$ alkyl, 3,3,3-trifluoropropyl, aralkyl or aryl;

Y is —(CR$^2$R$^3$)$_k$CR$^4$R$^5$CR$^6$R$^7$(CR$^8$R$^9$)$_h$—;

R$^1$ is C$_1$ to about C$_8$ alkyl or aryl;

R$^2$ to R$^9$ are each independently hydrogen, C$_1$ to about C$_8$ alkyl or aryl, provided that at least one of R$^4$ to R$^7$ is hydrogen;

R$^{10}$ is C$_1$ to about C$_8$ alkyl or C$_a$H$_{2a}$R$_f$;

m is 0, 1 or 2;

k and h are each independently an integer from 0 to 10, provided that at least one of k or h is zero;

a is an integer from 1 to about 10;

b is an integer from 1 to about 10;

c is 1, 2 or 3; and n is an integer greater than or equal to 2.

5. The compound of claim 4 wherein X is selected from the group consisting of: R$^1_m$SiY$_{4-m}$;

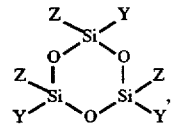 IA (b) (i)

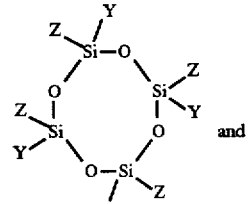 and IA (b) (ii)

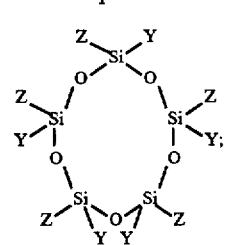 IA (b) (iii)

R$^1_m$Si(OSi(CH$_3$)$_2$Y)$_{4-m}$ and Y(CF$_2$)$_v$Y; and R$_f$ is CF$_3$, C$_2$F$_5$ or C$_3$F$_7$.

6. The compound of claim 5 selected from the group consisting of:

Si(CH$_2$CH$_2$SiCH$_3$(CH$_2$CF$_3$)$_2$)$_4$;
Si(CH$_2$CH$_2$SiCH$_3$(OCH$_2$(CF$_2$)$_2$CF$_3$)$_2$)$_4$;
Si(OSi(CH$_3$)$_2$CH$_2$CH$_2$SiCH$_3$(OCH$_2$CF$_3$)$_2$)$_4$;
Si(OSi(CH$_3$)$_2$CH$_2$CH$_2$SiCH$_3$(OCH$_2$(CF$_2$)$_2$CF$_3$)$_2$)$_4$;
Si(OSi(CH$_3$)$_2$CH$_2$CH$_2$CH$_2$SiCH$_3$(OCH$_2$CF$_3$)$_2$)$_4$;
(CF$_3$CH$_2$O)$_2$CH$_3$SiCH$_2$CH$_2$(CF$_2$)$_6$CH$_2$CH$_2$SiCH$_3$(OCH$_2$CF$_3$)$_2$;
(CF$_3$(CF$_2$)$_2$CH$_2$O)$_2$CH$_3$SiCH$_2$CH$_2$(CF$_2$)$_6$CH$_2$CH$_2$SiCH$_3$(OCH$_2$(CF$_2$)$_2$CF$_3$)$_2$;
(CF$_3$CH$_2$O)$_2$CH$_3$Si(CH$_2$)$_6$(CF$_2$)$_6$(CH$_2$)$_6$SiCH$_3$(OCH$_2$CF$_3$)$_2$;
Si(CH$_2$CH$_2$Si(CH$_2$CH$_2$CF$_2$CF$_3$)(OCH$_2$CF$_3$)$_2$)$_4$;
Si(CH$_2$CH$_2$Si(CH$_2$CH$_2$CF$_2$CF$_3$)(OCH$_2$(CF$_2$)$_2$CF$_3$)$_2$)$_4$;

Si(OSi(CH$_3$)$_2$CH$_2$CH$_2$Si(CH$_2$CH$_2$CF$_2$CF$_3$)(OCH$_2$CF$_3$)$_2$)$_4$;

Si(OSi(CH$_3$)$_2$CH$_2$CH$_2$Si(CH$_2$CH$_2$CF$_2$CF$_3$)(OCH$_2$(CF$_2$)$_2$CF$_3$)$_2$)$_4$;

Si(OSi(CH$_3$)$_2$CH$_2$CH$_2$CH$_2$Si(CH$_2$CH$_2$CF$_2$CF$_3$)(OCH$_2$CF$_3$)$_2$)$_4$;

(CF$_3$CH$_2$O)$_2$(CF$_3$CF$_2$CH$_2$CH$_2$)SiCH$_2$CH$_2$(CF$_2$)$_6$CH$_2$CH$_2$Si(CH$_2$CH$_2$CF$_2$CF$_3$)(OCH$_2$CF$_3$)$_2$;

(CF$_3$(CF$_2$)$_2$CH$_2$O)$_2$(CF$_3$CF$_2$CH$_2$CH$_2$)SiCH$_2$CH$_2$(CF$_2$)$_6$CH$_2$CH$_2$Si (CH$_2$CH$_2$CF$_2$CF$_3$)(OCH$_2$(CF$_2$)$_2$CF$_3$)$_3$;

(CF$_3$CH$_2$O)$_2$(CF$_3$CF$_2$CH$_2$CH$_2$)Si(CH$_2$)$_6$(CF$_2$)$_6$(CH$_2$)$_6$Si (CH$_2$CH$_2$CF$_2$CF$_3$)(OCH$_2$CF$_3$)$_2$; and cyclo-((CH$_3$)(CF$_3$CH$_2$O)$_2$CH$_3$SiCH$_2$CH$_2$)SiO)$_4$;

cyclo-((CH$_3$)(CF$_3$CH$_2$O)$_2$CH$_3$SiCH$_2$CH$_2$CH$_2$)SiO)$_4$;

cyclo-((CH$_3$)(CF$_3$CH$_2$O)$_2$CH$_3$SiCH$_2$CH$_2$CH$_2$)SiO)$_5$; and cyclo-((CH$_3$)(CF$_3$(CF$_2$)$_2$CH$_2$O)$_2$SiCH$_2$CH$_2$)SiO)$_4$.

7. A compound having the formula

   II wherein:

d is 1, 2 or 3;

e is an integer from 2 to about 10;

f is an integer from 2 to about 10;

R$^{10}$ is C$_1$ to about C$_8$ alkyl or C$_a$H$_{2a}$R$_f$;

R$_f$ has up to about 18 carbon atoms and is selected from the group consisting of:
 (a) C$_1$ to about C$_{18}$ perfluoroalkyl;
 (b) —[CF$_2$CF(CF$_3$)O]$_r$—CF$_2$—CF$_2$—CF$_3$, wherein r is an integer of at least 1;
 (c) —CF$_2$—(CF$_2$—O)$_q$—CF$_3$, wherein q is an integer of at least 2; and
 (d) —CH$_2$—C(CF$_3$)$_2$—CF$_2$—CF$_2$—CF$_3$;

wherein up to 50% of the fluorine of the R$_f$ group is optionally substituted with hydrogen;

a is an integer from 1 to about 10.

8. The compound of claim 7 wherein R$^{10}$ is C$_a$H$_{2a}$R$_f$.

9. The compound of claim 8 selected from the group consisting of:

Si(CH$_2$CH$_2$CH$_2$Si(CH$_3$)$_2$CH$_2$CH$_2$CH$_2$Si(OCH$_2$CH$_3$)$_3$)$_4$;

Si(CH$_2$CH$_2$CH$_2$Si(CH$_3$)$_2$CH$_2$CH$_2$CH$_2$Si(OCH$_2$CF$_3$)$_3$)$_4$;

Si(CH$_2$CH$_2$CH$_2$SiCH$_3$(CH$_2$CH$_2$CH$_2$Si(OCH$_2$CH$_3$)$_3$)$_2$)$_4$;

Si(CH$_2$CH$_2$CH$_2$SiCH$_3$(CH$_2$CH$_2$CH$_2$Si(OCH$_2$CF$_3$)$_3$)$_2$)$_4$; and Si(CH$_2$CH$_2$CH$_2$Si(CH$_2$CH$_2$CH$_2$Si(OCH$_2$CF$_3$)$_3$)$_3$)$_4$.

10. An oligomeric compound having the formula $$Si(OC_aH_{2a}R_f)_{4-z}O_{z/2}$$   I wherein:

z is a number from 0.5 to 3.0;

a is an integer from 1 to about 10; and

R$_f$ has up to about 18 carbon atoms and is selected from the group consisting of:
 (a) C$_1$ to about C$_{18}$ perfluoroalkyl;
 (b) —[CF$_2$CF(CF$_3$)O]$_r$—CF$_2$—CF$_2$—CF$_3$, wherein r is an integer of at least 1;
 (c) —CF$_2$—(CF$_2$O)$_q$—CF$_3$, wherein q is an integer of at least 2; and
 (d) —CH$_2$—C(CF$_3$)$_2$—CF$_2$—CF$_2$—CF$_3$;

wherein up to 50% of the fluorine of the R$_f$ group is optionally substituted with hydrogen.

11. The compound of claim 10 wherein R$_f$ is CF$_3$, C$_2$F$_5$, or C$_3$F$_7$, and a is 1 or 2.

12. An oligomeric compound having the formula

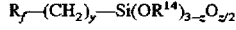   IV wherein:

z is a number from 0.5 to 2.5;

y is an integer from 2 to about 10;

each R$^{14}$ is independently C$_1$ to about C$_8$ alkyl, C$_1$ to about C$_{10}$ carboxy, C$_1$ to about C$_{10}$ fluorocarboxy or C$_a$H$_{2a}$R$_f$;

a is an integer from 1 to about 10; and

R$_f$ has up to about 18 carbon atoms and is selected from the group consisting of:
 (a) C$_1$ to about C$_{18}$ perfluoroalkyl;
 (b) —[CF$_2$CF(CF$_3$)O]$_r$—CF$_2$—CF$_2$—CF$_3$, wherein r is an integer of at least 1;
 (c) —CF$_2$—(CF$_2$—O)$_q$—CF$_3$, wherein q is an integer of at least 2; and
 (d) —CH$_2$—C(CF$_3$)$_2$—CF$_2$—CF$_2$—CF$_3$;

wherein up to 50% of the fluorine of the R$_f$ group is optionally substituted with hydrogen.

13. The oligomeric compound of claim 12 wherein R$_f$ is C$_6$F$_{13}$, n-C$_8$F$_{17}$ or n-C$_{10}$F$_{21}$, and a is 1 or 2.

* * * * *